US007913691B2

(12) United States Patent
Farrugia

(10) Patent No.: US 7,913,691 B2
(45) Date of Patent: Mar. 29, 2011

(54) SESSION-BY-SESSION ADJUSTMENTS OF A DEVICE FOR TREATING SLEEP DISORDERED BREATHING

(75) Inventor: Steven Paul Farrugia, Lugarno (AU)

(73) Assignee: ResMed Limited, Bella Vista, NSW (AU)

( * ) Notice: Subject to any disclaimer, the term of this patent is extended or adjusted under 35 U.S.C. 154(b) by 1287 days.

(21) Appl. No.: 10/597,291

(22) PCT Filed: Feb. 10, 2005

(86) PCT No.: PCT/AU2005/000174
§ 371 (c)(1),
(2), (4) Date: Jul. 19, 2006

(87) PCT Pub. No.: WO2005/077447
PCT Pub. Date: Aug. 25, 2005

(65) Prior Publication Data
US 2008/0053440 A1    Mar. 6, 2008

Related U.S. Application Data

(60) Provisional application No. 60/543,491, filed on Feb. 11, 2004.

(51) Int. Cl.
*F16K 31/02*    (2006.01)
(52) U.S. Cl. .............. 128/204.23; 128/204.21

(58) Field of Classification Search ............. 128/204.18, 128/204.21–204.23, 204.26
See application file for complete search history.

(56) References Cited

U.S. PATENT DOCUMENTS

| 5,203,343 | A | * | 4/1993 | Axe et al. ............... 600/538 |
| 5,458,137 | A | * | 10/1995 | Axe et al. ............... 128/204.23 |
| 5,803,066 | A | * | 9/1998 | Rapoport et al. ........ 128/204.23 |
| 2002/0095076 | A1 | * | 7/2002 | Krausman et al. .......... 600/323 |

FOREIGN PATENT DOCUMENTS

| EP | 0722747 | 7/1996 |
| WO | 92/22244 | 12/1992 |
| WO | 00/67827 | 11/2000 |
| WO | 00/74755 | * 12/2000 |

* cited by examiner

*Primary Examiner* — Steven O Douglas
*Assistant Examiner* — Kristen C Matter
(74) *Attorney, Agent, or Firm* — Gottlieb Rackman & Reisman, PC

(57) ABSTRACT

A method is disclosed for operating a device that treats sleep disordered breathing (SDB) during successive treatment sessions; where the device provides continuous positive airway pressure during sleep. The method comprises the steps of applying a constant treatment pressure during a first session (20) and deriving a sleep disorder index (SDI) (22) representative of the number of SDB episodes that occurred during the first session. If the treatment pressure should be increased based on the SDI, it is increase during a second, subsequent session (24).

49 Claims, 4 Drawing Sheets

SESSION-BY-SESSION ADJUSTMENTS OF A DEVICE FOR TREATING SLEEP DISORDERED BREATHING

FIELD OF THE INVENTION

This application claims the benefit of U.S. provisional application No. 60/543,491 filed on Feb. 11, 2004. The invention relates to devices for treatment of sleep disordered breathing (SDB). More specifically, the invention relates to a device for detecting SDB events in the presence of a continuous positive airway pressure and determining an appropriate adjustment to the airway pressure in response to detected SDB events.

BACKGROUND OF THE INVENTION

The present invention relates to the diagnosis and treatment of partial or complete upper airway occlusion, a condition in which the upper airway collapses, particularly under the reduced pressure generated by inhalation. This is most likely to happen during unconsciousness, sleep or anesthesia.

A particular application of the present invention is to the diagnosis and/or treatment of snoring and sleep apnea. Sleep apnea is characterized by complete occlusion of the upper airway passage during sleep while snoring is characterized by partial occlusion. An obstructive sleep apnea sufferer repeatedly chokes on their tongue and soft palate throughout an entire sleep period, resulting in lowered arterial blood oxygen levels and poor quality of sleep. It should be realized that although the following specification discusses sleep apnea in detail, the present invention also applies to the diagnosis and treatment of other forms of upper airway disorders.

The application of continuous positive airway pressure (CPAP) has been used as a means of treating the occurrence of obstructive sleep apnea. The patient is connected to a positive pressure air supply by means of a mouth and nose mask, nose mask only or nasal prongs. The air supply breathed by the patient is at all times at slightly greater than atmospheric pressure. For example, therapeutic pressures will typically be within the range of 4 $cmH_2O$ to 20 $cmH_2O$. It has been found that the application of continuous positive airway pressure (CPAP) provides what can be described as a "pneumatic splint", supporting and stabilizing the upper airway and thus eliminating the occurrence of upper airway occlusions. It is effective in eliminating both snoring and obstructive sleep apnea, and in many cases is effective in treating central and mixed apnea.

The airway pressure required for effective CPAP therapy differs from patient to patient. In order to discover the airway pressure which is most effective for a particular individual, the practice has been for the patient to undergo two sleep studies at an appropriate observation facility such as a hospital, clinic or laboratory. The first night is spent observing the patient in sleep and recording selected parameters such as oxygen saturation, chest wall and abdominal movement, air flow, expired $CO_2$, ECG, EEG, EMG and eye movement. This information can be interpreted to diagnose the nature of the sleep disorder and confirm the presence or absence of apnea and, where present, the frequency and duration of apneic episodes and extent and duration of associated oxygen desaturation. Apneas can be identified as obstructive, central or mixed. The second night is spent with the patient undergoing nasal CPAP therapy. When apnea is observed, the CPAP setting is increased to prevent apneas. The pressure setting at the end of the sleep period, i.e., the maximum used, is deemed to be the appropriate setting for that patient.

For a given patient in a given physical condition, various stages of sleep will require different minimum pressures to prevent occlusions. Furthermore, these various pressures will, in fact, vary from day to day depending upon the patient's physical condition, for example, nasal congestion, general tiredness, and effects of drugs such as alcohol, as well as the patient's sleeping posture. Thus the appropriate pressure found in the laboratory is necessarily the maximum of all these minimum pressures for that particular night and is not necessarily the ideal pressure for all occasions nor for every night. It will generally be higher than necessary for most of the night.

Also, a patient must be able to operate a CPAP system to deliver appropriate airway pressure at home where their general physical condition or state of health may be quite different from that in the sleep clinic, and will certainly vary from day to day. The patient's physical condition often improves due to CPAP therapy. It is often the case that after a period of therapy the necessary airway pressure can be reduced by some amount while still preventing the occurrence of obstructive sleep apnea.

The long term effects of CPAP therapy are unknown so it is desirable to keep the airway pressure as low as practicable, particularly if a patient requires long term treatment. Lower airway pressures also result in a lower face mask pressure which is generally more comfortable for the patient. It has been found that CPAP induces patients to swallow and this inducement to swallow can be reduced by lowering the airway pressure. Thus it is desirable to use the lowest practicable airway pressure that is effective in preventing airway occlusion during CPAP therapy for the comfort and possibly the long term safety of the patient. Also, a lower airway pressure requires less energy consumption and a less complex and therefore less expensive apparatus, which is also generally quieter.

Low airway pressures are also desirable before and during the early stage of each sleep period as the increased comfort of an initially lower airway pressure allows the patient to more easily fall asleep. When a patient undergoing CPAP opens their mouth with pressurized air being forced through the nose, the pressured air exits out of the mouth producing an unpleasant sensation. This can occur when the patient puts on the mask connected to the pressured air supply before falling asleep and some patients will therefore leave the mask off for as long as possible and may in fact fall asleep without wearing the mask and therefore without the benefits of the CPAP therapy.

In addition to the problems associated with administering CPAP therapy there exists the inconvenience and cost of diagnosis which may be undertaken by overnight observation at a sleep clinic or the like. Hence a simple means whereby a patient's apnea problem can be diagnosed at home without supervision is clearly desirable as well as a CPAP device which will deliver a continuously minimum appropriate pressure for substantially the entire period of therapy.

Although diagnosis in a sleep clinic as outlined above is beneficial, it has some deficiencies. A patient is likely not to sleep in a fully relaxed state in an unfamiliar environment and a single night is insufficient to obtain a pressure setting that will be optimal in the long run. Thus home therapy at the pressure setting arrived at in this way is likely to be less than 100% effective on some occasions and higher than necessary for a substantial portion of the time. The cost and inconvenience of a sleep study in a hospital setting are to be avoided if possible.

A skilled physician can usually recognize the symptoms of sleep apnea from questioning and examining a patient. Where no other indications are present there is very little risk in attempting nasal CPAP therapy without further testing as the treatment is fail safe and non-invasive. However, a very useful intermediate step would be to analyze the pattern of respiratory waveforms (e.g., pressure, flow or sound) over one or more full nights of sleep. Interpretation of these patterns together with questioning and examination will, in many cases, provide sufficient confirmation of apnea to prescribe nasal CPAP therapy. If nasal CPAP eliminates the symptoms of day time sleepiness (as assessed by the patient) and of apneic snoring patterns (as assessed by analysis of recorded respiratory sounds while on nasal CPAP), the treatment can be continued. Further check-ups can be conducted at intervals recommended by the physician.

In the most general form of a CPAP treatment device, the intermediate step before the device attempts CPAP pressure increases is to analyze the patterns of the respiratory parameters that can be obtained from sensors, such as a pressure sensor or flow sensor. As those skilled in the art will recognize, these parameters include, in addition to acoustic rate of breathing, inhaled/exhaled air volume and inhaled/exhaled air flow rate, and provide comprehensive information for the physician to assess the patient's condition. This additional information, for example, generated by a pressure transducer, is available at additional cost and complexity. Similar information related to airflow may be estimated from the speed of or current supplied to the blower of the apparatus that is supplying the pressure to the mask in a system where pressure changes are generated by changing the speed of the blower. Examples of such an implementation are disclosed in commonly owned U.S. Pat. Nos. 5,740,795, 6,332,463 and 6,237,593, the disclosures of which are hereby incorporated by reference.

The measurement of other parameters would provide further information to assist diagnoses, and the acoustic and/or other respiratory recordings described above can readily be used in conjunction with other monitors such as ECG and/or pulse oximetry. Suitable monitors are available to measure both these parameters in the home. The correlation between reduced oxygen saturation and apnea is sufficiently well established to infer oxygen desaturation from the confirmation of an apneic event.

One index determined from these parameters is the Apnea Hypopnea Index. The Apnea Hypopnea Index ("AHI") is an indicator of severity of a patient's sleep disordered breathing. The AHI is determined by adding the total number of apneas and hypopneas the patient experienced over a particular time period, such as during a sleep clinic study. Various forms of AHI index are known by those skilled in the art.

However, in automated devices, sophisticated sensors and associated algorithms for detecting SDB events and determining an appropriate response to the detected events add a level of complexity to the device that may increase the cost, potentially making them too expensive for some patients. Thus there is a need for a device that can accurately adjust the therapeutic pressures in response to SDB events to alleviate the events but utilizing minimum hardware and minimized methodology for controlling the hardware.

OBJECTS AND SUMMARY OF THE INVENTION

It is an objective of the invention to provide a device that can detect SDB events and automatically and effectively determine an appropriate pressure response.

It is an objective of the invention to provide such a device that minimizes the pressure treatment but assures the provision of a minimum level of support necessary to treat the patient.

It is still a further objective to provide such a device with minimal components to ensure that it is inexpensive and cost-effective to develop and manufacture.

The invention is a device for detecting SDB events and adjusting pressure to prevent such events on a session-by-session basis, such as night by night, rather than on a breath-by-breath basis. In the device, in a first session while providing a level of treatment pressure, an indicator of severity of SDB events is detected. For example, in the first session the device detects and records a total number of apneas and hypopneas. Preferably, the detection of such events does not result in a change to the treatment pressure during that session. In a subsequent session, the treatment pressure is adjusted based on what the device learned during the previous session. Thus, the historic SDB index from the previous session is compared to a threshold in a current session and the treatment pressure is currently adjusted based on the historic index. In other words, pressure changes in subsequent sessions may increase or decrease depending on the nature of the historic SDB indicator. For example, if the prior night's AHI is greater than a threshold of 8, the pressure is automatically increased for use during the new session. If the pressure is less than 8, the pressure may decrease or stay the same. In one embodiment, patterns in changes over several prior sessions, such as consecutive nights, are analyzed to automatically determine a pressure setting in a current session. For example, if the AHI is 0 for two consecutive nights, the pressure may be reduced for or in the next night's treatment.

In the preferred embodiment of the invention, an AHI index is determined from a flow signal which is preferably calculated from speed of the blower or current to the blower without use of a differential pressure transducer type flow sensor. Similarly, it is preferred that no pressure sensor be used in the setting of the pressure in the mask. Such a configuration assists in meeting the objectives as previously described. Further aspects of the invention are described in more detail herein.

BRIEF DESCRIPTION OF THE FIGURES

To satisfy the recited objectives, a description of the invention is provided with reference to appended drawings that depict typical embodiments of the invention and are not intended to limit the scope of the invention, in which.

DESCRIPTION OF THE INVENTION

Figure 1:
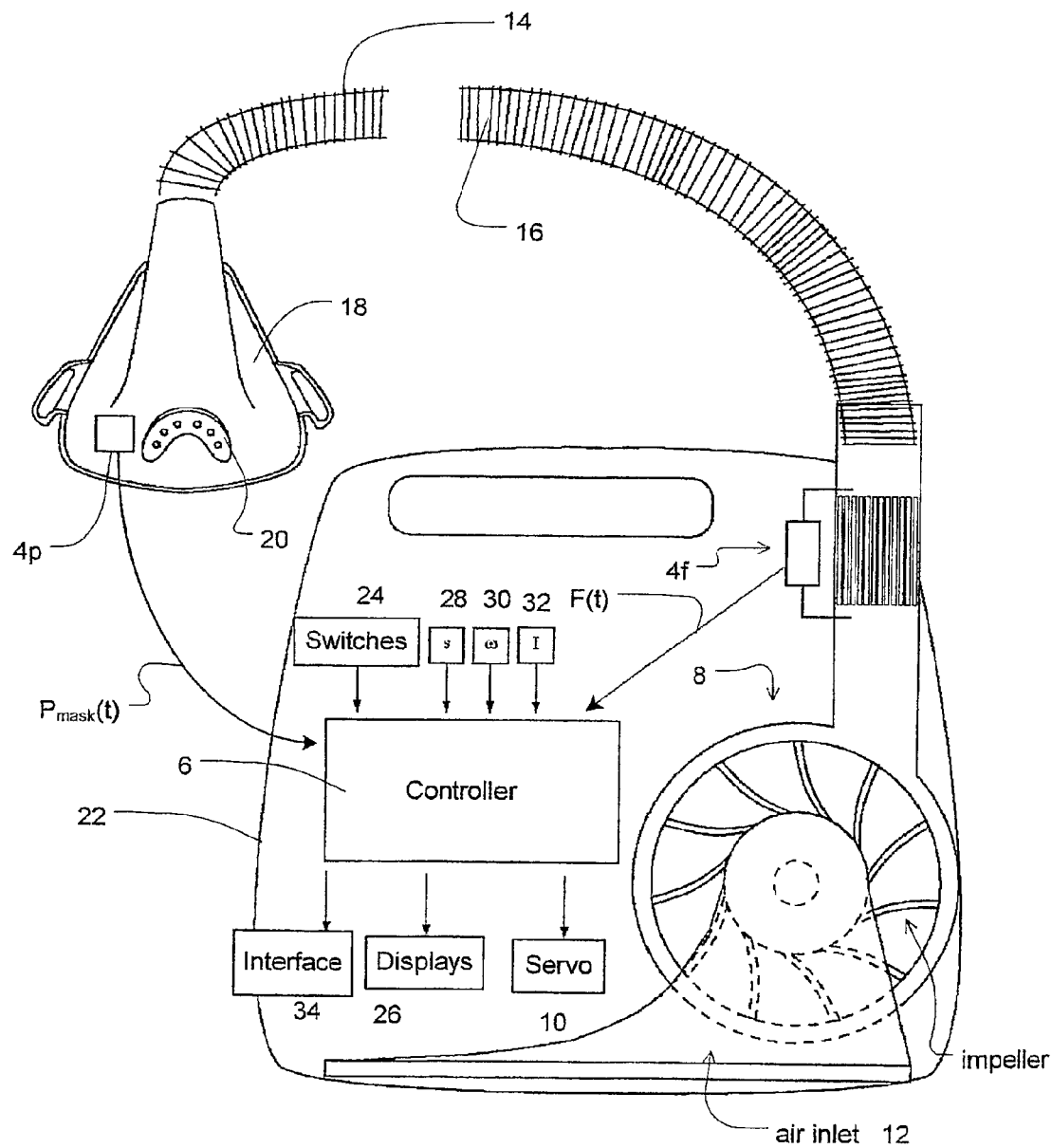
FIG. 1 depicts the structure of an embodiment of a pressure treatment apparatus suitable for implementing the methods of the current invention.

In reference to FIG. 1, mask flow is measured using a flow sensor 4*f* and/or pressure sensor 4*p* with a pneumotachograph and differential pressure transducer or similar device. A flow signal F(t) is derived and mask pressure is measured at a pressure tap using a pressure transducer to derive a pressure signal $P_{mask}(t)$. The pressure sensor 4p and flow sensor 4f have only been shown symbolically in FIG. 1 since those skilled in the art would understand how to measure flow and pressure. Flow F(t) and pressure $P_{mask}(t)$ signals are sent to a controller or microprocessor 6 which then determines how to adjust the blower. Alternatively, it is preferred that a flow signal f(t) and pressure signal $P_{mask}(t)$ be estimated or calculated in relation to the blower motor by monitoring power supplied to the motor and/or the speed of the motor as disclosed in U.S. Pat. Nos. 5,740,795, 6,332,463 or 6,237,593, without the provision of flow and pressure sensors as described above.

The controller 6 is configured and adapted to implement the methodology described in more detail herein and may include integrated chips, a memory and/or other instruction or data storage medium. For example, programmed instructions with the control methodology may be coded on integrated chips in the memory of the device (e.g., firmware) or loaded as software.

The pressure delivery device includes a blower 8, which preferably is an impellor. The impellor 8 is controlled by a servo 10, receives ambient air through an inlet 12 and delivers pressurized air through an outlet 14 defined by an air delivery conduit 16 and a mask 18 with an integrated exhaust vent 20. The impellor, motor, and controller assembly define a blower assembly and are located within the blower housing 22. Various switches 24 and displays 26 are provided in the blower housing. A number of sensors are provided within the blower to monitor, among other things, snore 28, motor speed 30, and motor current 32. Various devices known in the art can serve as these types of sensors. A communication interface 34 allows data to be transferred between the apparatus and an external device, such as a computer or controller.

Preferably, the device delivers a generally constant therapeutic level of continuous positive airway pressure (CPAP) during any given treatment session. However, consistent with the control principles of the invention as described herein, other types of pressure treatment may be implemented in the apparatus, such as bi-level CPAP treatment or other variants of natural patient-synchronized pressure changes.

A. Control of Pressure Adjustments Based on Historic AHI Determinations

Figure 2:
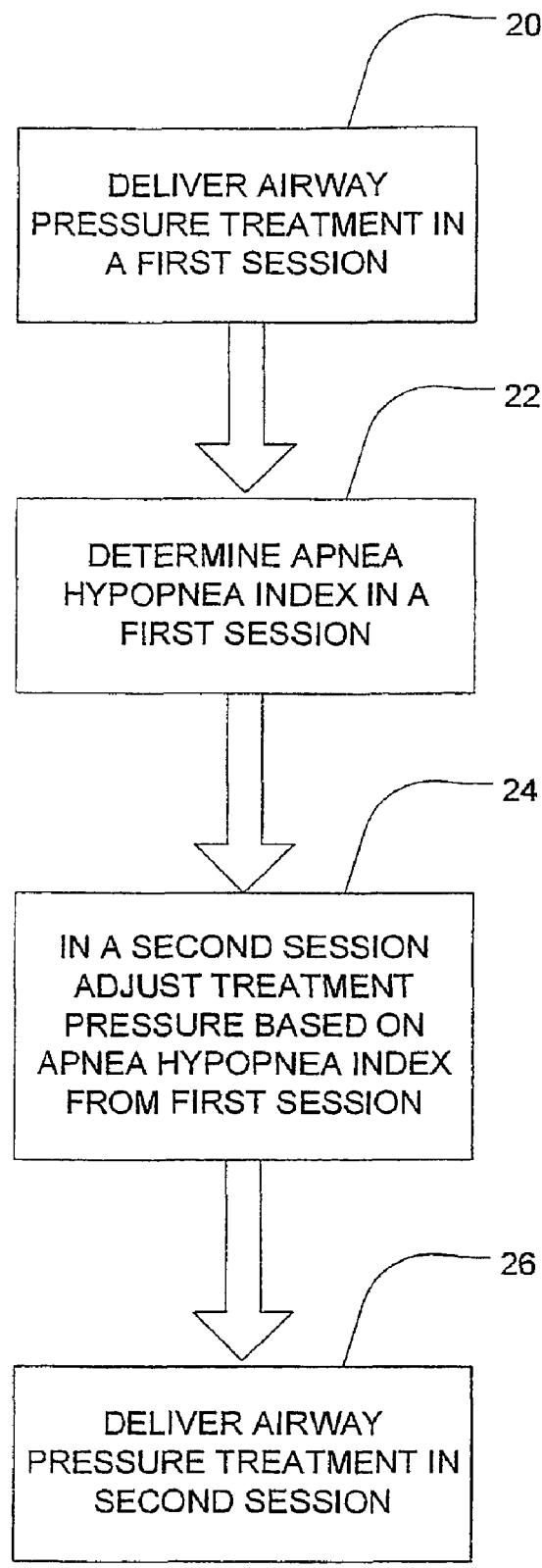
FIG. 2 is a flow chart of steps in a methodology for the control of a pressure treatment apparatus for making pressure adjustments during a treatment session based on apnea/hypopnea (AHI) indices taken from an earlier treatment session.

As illustrated in FIG. 2, the pressure treatment apparatus implements control based on historic AHI determinations. As shown in step 20, airway pressure treatment is provided to the patient during a first treatment session. In such a session, in the absence of historic AHI, the pressure treatment level will be set to a default low or minimum level, or a level prescribed by a physician or clinician. Preferably, no adjustments to the treatment pressure are made to change the level of therapy in response to a current detection of an SDB event during the current session. During the treatment session, in step 22, sleep disordered breathing events are detected and an index of these events is determined. Preferably, apnea and hypopnea events are detected and an AHI, the AHI being initialized for the current session, is incremented by the number of such detected events. In step 24, a new or subsequent treatment session is initiated with the apparatus. In this subsequent session, a therapeutic level of the treatment is set automatically as a function of the SDB event related index that was determined in the prior treatment session.

In the preferred embodiment of the invention, each of the previously described treatment sessions is a different night's treatment with the device. Thus, an AHI may be recorded during use of the treatment apparatus during a single night and saved at the conclusion of the session. This saved AHI may then be utilized to set the treatment pressure in the next use of the device, such as during the next night. To distinguish such sessions, the device may be configured to store the AHI on power down. Then it will utilize a previously recorded AHI, if it exists, in setting the treatment pressure after the device is powered on but before or as treatment is commenced. Alternatively, other schemes for ensuring the use of an AHI from a previously recorded session may be implemented. In one alternative scheme, date and/or time of every determined AHI from all sessions are recorded and stored. During a subsequent use, checking is performed for the most recent AHI. Similarly, this may be implemented by checking the date of an AHI against an internal clock to permit the use of a previous day's AHI in setting treatment pressure.

While additional pressure treatment adjustments may be made in a current session based on a current AHI determination or on detection of an SDB related event, it is preferred that no such adjustments be made until a subsequent session. Similarly, the ramping of pressure from a low pressure up to the set therapeutic treatment pressure such that the patient can fall asleep before reaching the therapeutic level may also be implemented by the device.

B. Determination of an Apnea Hypopnea Index (AHI) in a First Session

Figure 3:
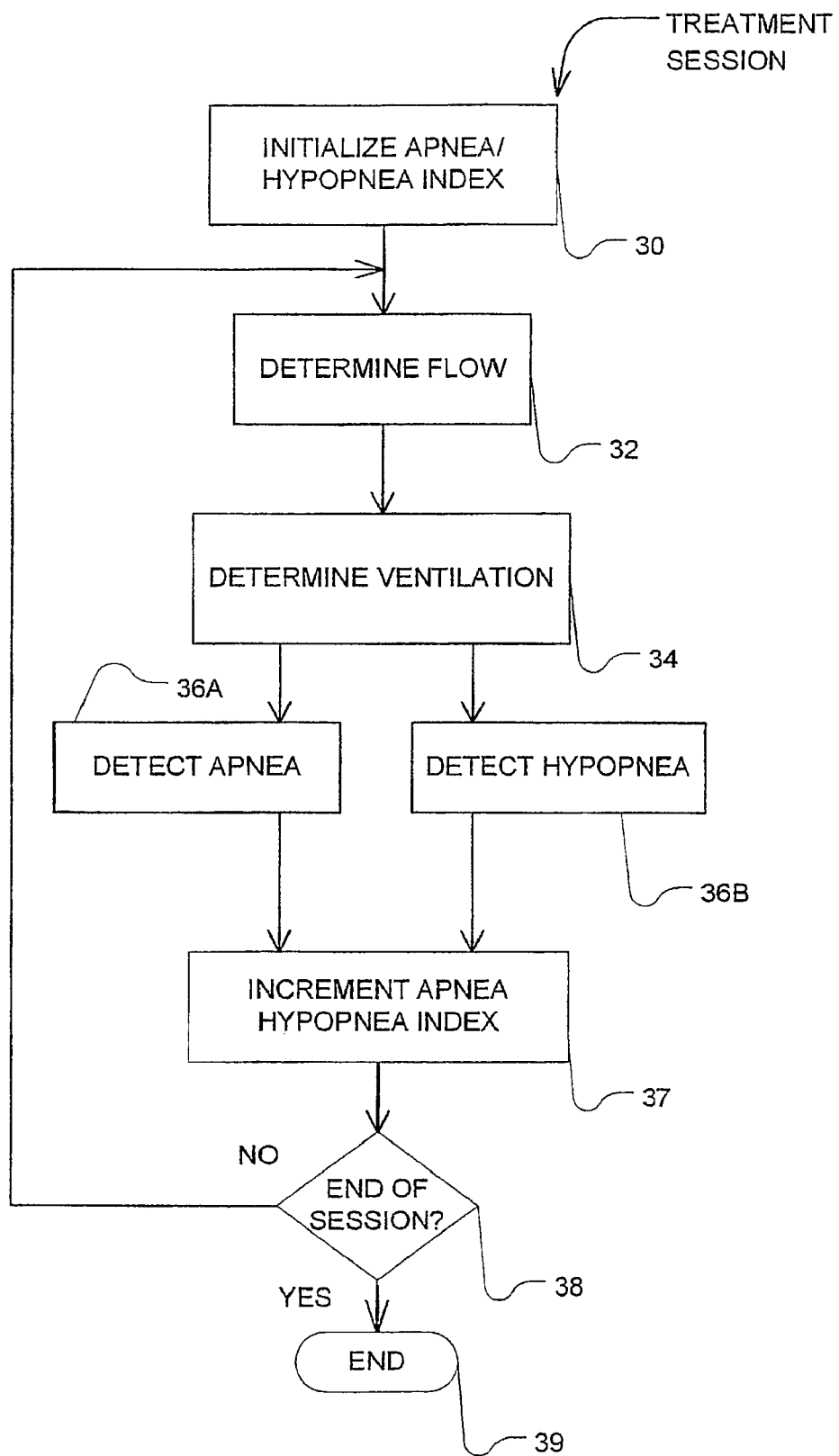
FIG. 3 is a more detailed flow chart of steps in a methodology for the control of a pressure treatment apparatus to determine an AHI during a treatment session.

As previously noted, the pressure treatment device preferably detects sleep disordered breathing events including apneas and hypopneas, by determining an Apnea-Hypopnea Index. Optionally, other SDB related indices may be used, for example, an apnea index, a hypopnea index or some other SDB related index. The preferred determination methodology is illustrated in the flow chart of FIG. 3. At the beginning of a treatment session with the device, a current SDB index or AHI is reset or initialized in step 30. During the delivery of pressure treatment, flow is continuously measured or determined in step 32. With flow information or the flow signal (e.g., from a differential pressure transducer or derived from blower speed or power to the blower motor), measures of ventilation (e.g., an average flow determined over a period of time) are calculated in a step 34.

Preferably, these ventilation measures include a short term measure and a long term measure. In one embodiment, a suitable recent ventilation measure or a short term average may be a low pass filtered flow signal utilizing a low pass filter having a time constant which is short with respect to the duration of a breath, e.g., about 2 to 8 seconds. A suitable longer term ventilation or longer term average measure of flow may be a low pass filtered flow signal utilizing a low pass filter having a time constant which is long with respect to the duration of a breath, e.g., about 110 seconds.

These ventilation measures, including a short term measure and a long term measure, are for purposes of comparing a more recent average measure with a longer term average. From the results of such a comparison, either apneas or hypopneas may be detected in steps 36A and/or 36B respectively. For example, in detecting a hypopnea, if the short term average measure falls below the longer term average such that it is less than 50% of the longer term average, a hypopnea may be tallied or detected. Similarly, if the short term average falls below the longer term average such that it is less than 20% of the longer term average, an apnea may be tallied or detected.

In one embodiment of the invention an AHI scoring scheme may be implemented as follows:

i. An apnea is scored if a 2 second moving average ventilation drops below 25% of a recent average ventilation (time constant=100 s) for at least 10 consecutive seconds, ii. A hypopnea is scored if an 8 second moving average drops below 50% but not more than 25% of the recent average ventilation for 10 consecutive seconds.

Those skilled in the art will recognize other methods or modifications for detecting hypopneas or apneas and determining an AHI or an SDB index which will otherwise indicate severity in the patient's SDB symptoms.

After detecting either an apnea or a hypopnea event, an AHI may be incremented in step 37. After incrementing the AHI, the system determines whether the session has ended at step 38. At this point, the system terminates at step 39. If the session is ongoing, the system cycles back to step 32 to continue detecting apnea and hypopnea events and incrementing the AHI.

The total of these detected apneas and hypopneas for any given session would make up the AHI used in the adjustment of treatment pressure in a subsequent session. Preferably, the AHI is determined by adding the total number of apneas and hypopneas the patient experienced over a treatment period covering a single night. Optionally, the AHI may be a function of time such as an average hourly AHI determined over the total time for any given treatment session with the device such as a period of sleep or a single night of sleep.

Figure 4:
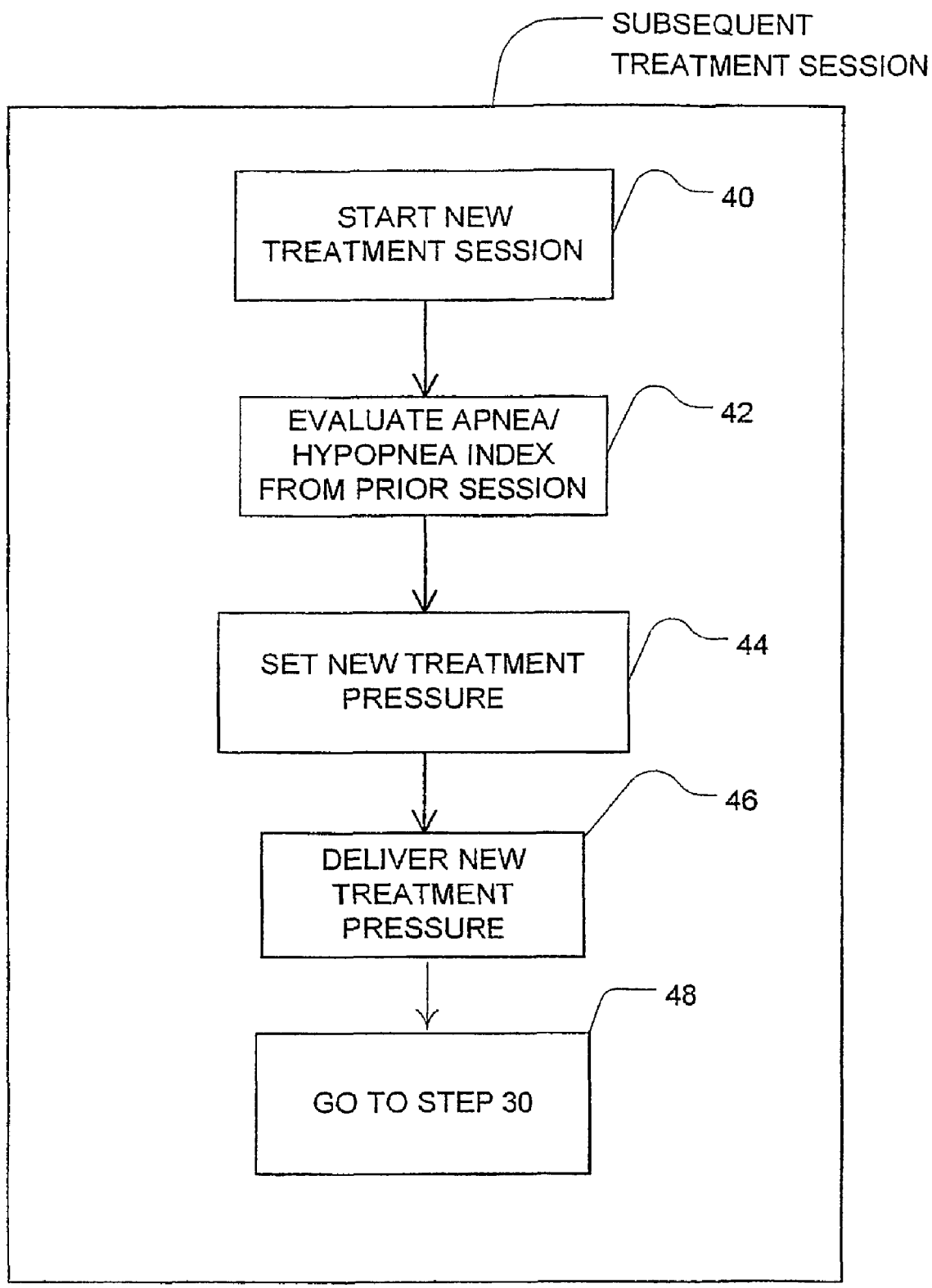
FIG. 4 is a more detailed flow chart of steps in a methodology for the control of the adjustment of pressure treatment in a subsequent session based upon an AHI taken during a prior treatment session.

C. Adjustment of Treatment Pressure in Response to AHI in a Subsequent Session As previously noted, preferably automated adjustments to the therapeutic level of the treatment pressure are only made or only take effect for treatment in a subsequent session or subsequent night of treatment based on an AHI determined in a prior session or previous night of treatment. That is, the automated dynamic pressure changes are on a night-by-night basis rather than a breath-by-breath basis. Thus, the device implements an algorithm for adjusting the treatment pressure in a subsequent session. For example, as illustrated in FIG. 4, after starting a new or entering a treatment session in step 40, the device may then evaluate a previously recorded AHI in an evaluation step 42. Based on the detected AHI from a prior session a new treatment pressure will be set. Optionally, for a first use or first session, the AHI may have a default of 0 such that no changes to the treatment pressure will be implemented in the first session. Similarly, a default pressure setting for the first use may be a low non-therapeutic value (e.g., about 1-3 $cmH_2O$) or some other physician or clinician set value in a therapeutic range of about 4-20 $cmH_2O$.

In evaluating the historic AHI in step 42, if a prior session results in no detected apneas or hypopneas or only a few (e.g., AHI=0 or less than 8), no pressure changes will be implemented and the treatment pressure setting will remain from the prior session. Alternatively, for purposes of determining the minimum pressure necessary to prevent SDB, for an AHI of 0 or an AHI of less than 8 from the prior session, the device may lower the pressure in the new session. In lowering the pressure, the device may decrement the pressure by a fixed amount, (e.g., 0.25 $cmH_2O$) which is preferably lower than the pressure increase although they may be the same. Thus, in setting the treatment pressure in step 44, the new pressure for the current setting will be the pressure from the prior session less the fixed decrement amount.

However, if the AHI from the prior session is greater than 0 or greater than some low non-adjustment range (e.g., 1-8 events), the treatment pressure will automatically increment upwards since such an AHI score is an indication of the need for an increase in treatment. Thus, based on the high AHI from the previous night, the treatment pressure can be increased by some increment. The treatment pressure increase is performed with the intent to decrease the AHI towards a clinically desirable level in the subsequent night. The ideal treatment pressure will decrease the AHI to a clinically desirable level but not be so far in excess of the minimum required pressure that it induces unnecessary discomfort. Therefore, the quantum of the incremental pressure increase may vary depending upon the perceived clinical severity of the AHI. For example, the choice of incremental pressure increase may reflect the clinical observation that a relatively small increment will induce a clinically significant change where the patient has a relatively low AHI (e.g., a pressure increment of 0.5 $cmH_2O$ for an AHI in the range of 5-19) while a relatively larger increment will be appropriate to induce a clinically significant change where the patient has a relatively high AHI (e.g., a pressure increment of 2 $cmH_2O$ for an AHI of 40 or higher).

Referring to FIG. 4, in the treatment pressure setting step 44, the treatment pressure is automatically set for the new session to be the previous session's pressure setting plus the increment. The treatment pressure will then be delivered during the current session in step 46 and then, at step 48, the system cycles back to step 30 (FIG. 3) and again begins the process of determining a new AHI. The new AHI will affect the treatment pressure for the next session or treatment in the next night or future session. Such a scheme allows the device to adjust itself over an unlimited number of nights, while evolving with the needs of the patient.

In one embodiment, other schemes of adjustment of the pressure may be based on patterns of the AHI over more than a single night, such as two or more nights. For example, the pressure may be lowered if the AHI has been 0 for two or more consecutive sessions. Similarly, pressure may be increased only if the AHI in more than one consecutive night, for example, 2 or 3 nights, suggests a need for an increase. Preferably, any decay in pressure over time is slower than the increase in pressure over time.

Optionally, the device may be configured with an adaptation range that limits the changes to the treatment pressure that the device may automatically implement based on a previous night's AHI determination. The adaptation range may be a preset variable that is determined by a physician and preferably is not changed during the many treatment sessions with the user or patient. A default range may be set into the device in the absence of such a setting by a physician. For example, the physician may preset the adaptation range to a value of 10 $cmH_2O$. When a pressure change is implemented by the device, the range is checked to make certain that any increments attempted by the device never exceed the original pressure setting of the physician by the amount of the range. Thus, if the pressure is set to 5 $cmH_2O$ for the first session with a patient, and the adaptation range is set to 10 $cmH_2O$, any automated treatment pressure change that attempts to increment the treatment pressure beyond 15 $cmH_2O$ would be prevented. In addition, the device may be configured with an optional warning indicator to advise the patient or the physician of the attempted increase beyond the adaptation range.

A device that implements the above-described treatment scheme would have many benefits for SDB patients. For example, utilizing the described algorithm would be more cost effective when compared to more complex detection and adjustment schemes. Also, since the device can adjust on a night-by-night basis, it can provide adaptation for seasonal changes that may affect the patient's condition. It can also adapt with the patient's disease progression.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

What is claimed is:

1. A method of operating a device for treating sleep disordered breathing (SDB) during successive treatment sessions, wherein said device provides continuous positive airway pressure during sleep, the method comprising the steps of:
   applying a constant treatment pressure during a first session;
   deriving a sleep disorder index (SDI) representative of the number of SDB episodes that occurred during said first session;
   determining if said treatment pressure should be increased based upon the derived SDI; and
   increasing said treatment pressure during a second, subsequent session if it was determined during said first session that said treatment pressure should be increased,
   each of said first and second sessions occurring during a different night.

2. The method of claim 1 wherein said SDI is an apnea hypopnea index (AHI) that represents the number of apnea and hypopnea events during said first session.

3. The method of claim 2 wherein an AHI event is determined when a short term moving average of ventilation drops below a selected percentage of a long term average for a minimum period of time.

4. The method of claim 3 wherein a hypopnea event is determined when said short term average drops between a first and a second percentage of said long term average for a minimum period of time.

5. The method of claim 2 wherein if said AHI is less than a minimum number, then said treatment pressure is lowered in a subsequent session.

6. The method of claim 5 wherein the rate of increase in treatment pressure over successive sessions is greater than the rate of decrease in said treatment pressure over successive sessions.

7. The method of claim 2 wherein if said AHI is greater than a minimum number, then said treatment pressure is increased in a subsequent session.

8. The method of claim 2 wherein said treatment pressure is increased in a subsequent session by an amount that is a function of the magnitude of the derived AHI.

9. The method of claim 2 wherein said treatment pressure is increased only if said AHI was greater than a minimum number and said treatment pressure is less than a maximum value.

10. The method of claim 1 wherein an SDI event is determined when a short term moving average of ventilation drops below a selected percentage of a long term average for a minimum period of time.

11. The method of claim 1 wherein if said SDI is less than a minimum number, then said treatment pressure is lowered in a subsequent session.

12. The method of claim 11 wherein the rate of increase in treatment pressure over successive sessions is greater than the rate of decrease in said treatment pressure over successive sessions.

13. The method of claim 1 wherein if said SDI is greater than a minimum number, then said treatment pressure is increased in a subsequent session.

14. The method of claim 1 wherein said treatment pressure is increased in a subsequent session by an amount that is a function of the magnitude of the derived SDI.

15. The method of claim 1 wherein said treatment pressure is increased only if said SDI was greater than a minimum number and said treatment pressure is less than a maximum value.

16. A system for treating sleep disordered breathing (SDB) during successive treatment sessions, wherein the system provides continuous positive airway pressure during sleep, the system comprising:
   a blower and a blower controller;
   a mask for communicating pressurized air between said blower and a patient; and
   sensors for communicating signals indicative of pressure and flow to said controller, wherein said controller:
   controls a constant treatment pressure to be applied during a first session;
   derives a sleep disorder index (SDI) representative of the number of SDB episodes that occurred during said first session;
   determines if an increase in treatment pressure is required based upon said derived SDI; and
   controls an increase in said treatment pressure during a second, subsequent session if it was determined that an increase is required,
   each of said first and second sessions occurring during a different night.

17. The system of claim 16 wherein said SDI is an apnea hypopnea index (AHI) that represents the number of apnea and hypopnea events that occurred during said first session.

18. The system of claim 17 wherein said controller determines an apnea event when a short term moving average of ventilation drops below a long term moving average of ventilation for a minimum period of time.

19. The system of claim 17 wherein said controller determines a hypopnea event when said short term average drops between a first and a second percentage of said long term average for a minimum period of time.

20. The system of claim 17 wherein if said controller determines that said AHI is less than a minimum number, then said treatment pressure is lowered in said subsequent session.

21. The system of claim 20 wherein a rate of increase of treatment pressure in successive sessions is greater than a rate of decrease of pressure in successive sessions.

22. The system of claim 17 wherein if said AHI was less than a minimum number, then said controller maintains said treatment pressure in said subsequent session.

23. The system of claim 17 wherein if said AHI was greater than a minimum number, then said controller increases said treatment pressure in said subsequent session.

24. The system of claim 17 wherein said controller increases said treatment pressure in said subsequent session by an amount that is a function of the magnitude of said derived AHI.

25. The system of claim 17 wherein said controller increases said treatment pressure only if said AHI was greater than a minimum number and said treatment pressure was less than a maximum pressure.

26. The system of claim 16 wherein said controller determines an SDI event when a short term moving average of ventilation drops below a long term moving average of ventilation for a minimum period of time.

27. The system of claim 16 wherein if said controller determines that said SDI is less than a minimum number, then said treatment pressure is lowered in said subsequent session.

28. The system of claim 27 wherein a rate of increase of treatment pressure in successive sessions is greater than a rate of decrease of pressure in successive sessions.

29. The system of claim 16 wherein if said SDI was less than a minimum number, then said controller maintains said treatment pressure in said subsequent session.

30. The system of claim 16 wherein if said SDI was greater than a minimum number, then said controller increases said treatment pressure in said subsequent session.

31. The system of claim 16 wherein said controller increases said treatment pressure in said subsequent session by an amount that is a function of the magnitude of said derived SDI.

32. The system of claim 16 wherein said controller increases said treatment pressure only if said SDI was greater than a minimum number and said treatment pressure was less than a maximum pressure.

33. A system for treating sleep disordered breathing (SDB) during successive treatment sessions, wherein the system provides continuous positive airway pressure during sleep, the system comprising:
 a blower and a blower controller;
 a mask for communicating pressurized air between said blower and a patient; and
 sensors for communicating signals indicative of pressure and flow to said controller, wherein said controller:
 controls a constant treatment pressure to be applied during a first session;
 derives a sleep disorder index (SDI) representative of the number of SDB episodes that occurred during said first session;
 determines if an increase in treatment pressure is required based upon said derived SDI; and
 controls an increase in said treatment pressure during a second, subsequent session if it was determined that an increase is required,
 said first and second sessions being separate in that said blower is turned off between the sessions.

34. The system of claim 33 wherein said SDI is an apnea hypopnea index (AHI) that represents the number of apnea and hypopnea events that occurred during said first session.

35. The system of claim 34 wherein said controller determines an apnea event when a short term moving average of ventilation drops below a long term moving average of ventilation for a minimum period of time.

36. The system of claim 34 wherein said controller determines a hypopnea event when said short term average drops between a first and a second percentage of said long term average for a minimum period of time.

37. The system of claim 34 wherein if said controller determines that said AHI is less than a minimum number, then said treatment pressure is lowered in said subsequent session.

38. The system of claim 37 wherein a rate of increase of treatment pressure in successive sessions is greater than a rate of decrease of pressure in successive sessions.

39. The system of claim 34 wherein if said AHI was less than a minimum number, then said controller maintains said treatment pressure in said subsequent session.

40. The system of claim 34 wherein if said AHI was greater than a minimum number, then said controller increases said treatment pressure in said subsequent session.

41. The system of claim 34 wherein said controller increases said treatment pressure in said subsequent session by an amount that is a function of the magnitude of said derived AHI.

42. The system of claim 34 wherein said controller increases said treatment pressure only if said AHI was greater than a minimum number and said treatment pressure was less than a maximum pressure.

43. The system of claim 33 wherein said controller determines an SDI event when a short term moving average of ventilation drops below a long term moving average of ventilation for a minimum period of time.

44. The system of claim 33 wherein if said controller determines that said SDI is less than a minimum number, then said treatment pressure is lowered in said subsequent session.

45. The system of claim 44 wherein a rate of increase of treatment pressure in successive sessions is greater than a rate of decrease of pressure in successive sessions.

46. The system of claim 33 wherein if said SDI was less than a minimum number, then said controller maintains said treatment pressure in said subsequent session.

47. The system of claim 33 wherein if said SDI was greater than a minimum number, then said controller increases said treatment pressure in said subsequent session.

48. The system of claim 33 wherein said controller increases said treatment pressure in said subsequent session by an amount that is a function of the magnitude of said derived SDI.

49. The system of claim 33 wherein said controller increases said treatment pressure only if said SDI was greater than a minimum number and said treatment pressure was less than a maximum pressure.

* * * * *